United States Patent [19]
de Latour

[11] 3,934,192
[45] Jan. 20, 1976

[54] METHOD OF DETECTION OF IONS IN SOLUTION THAT ARE SUSCEPTIBLE TO AN APPLIED FORCE FIELD AND APPARATUS THEREFOR

[75] Inventor: Christopher de Latour, Arlington, Va.

[73] Assignee: Massachusetts Institute of Technology, Cambridge, Mass.

[22] Filed: Apr. 25, 1974

[21] Appl. No.: 464,263

[52] U.S. Cl............ 324/34 R; 23/230 R; 23/253 R; 222/420
[51] Int. Cl.²......................................... G01R 33/12
[58] Field of Search........ 324/34 R, 34 S; 23/230 R, 23/253 R; 222/420

[56] References Cited
UNITED STATES PATENTS
3,787,761   1/1974   Grossman et al.................. 324/34 S

OTHER PUBLICATIONS
Aleinikov et al., Deformation Effect & Liquid Dispersion Kinetics in a Magnetic Field; Inzhenerno – Fizicheskii Zhurnal; Vol. 19, No. 6, pp. 1118–1121, Dec. 1970.

Primary Examiner—Robert J. Corcoran
Attorney, Agent, or Firm—Arthur A. Smith, Jr.; Robert Shaw; Martin M. Santa

[57] ABSTRACT

A process wherein a solution is allowed to fall from the end of a capillary tube in the presence of a gradient field of an applied force field (magnetic or electric). If the fluid contains ions that are susceptible to the applied field, then the content of those ions can be correlated to the change in the specific characteristics of the capillary drop (i.e., the drop weight or equivalently the drop volume). This finds use as an assay technique for those susceptible ions, and it further can be used to give information as to the degree of susceptibility that the ions show to the applied force field.

32 Claims, 17 Drawing Figures

| SYMBOL | DESCRIPTION |
|---|---|
| $W_o$ | Weight of drop with no external field |
| $r$ | Radius of the capillary tube (cm) |
| $\gamma$ | Surface tension of the solution (dynes/cm) |
| $V_o$ | Volume of drop with no external field |
| $\rho$ | Density of the liquid (grams/cc) |
| $\rho_s$ | Density of medium surrounding the drop |
| $g$ | Acceleration due to gravity |
| $\phi(r/V^{1/3})$ | Dimensionless empirical function needed to correct Tate's law |
| $W_f$ | Weight of drop when an external field is applied |
| $V_f$ | Volume of drop with an external field applied |
| $X$ | Volume susceptibility of the liquid (dimensionless) |
| $X_s$ | Volume susceptibility of medium displaced by drop |
| $X_{air}$ | Volume susceptibility of the atmosphere |
| $F$ | Field intensity |
| $\nabla F$ | Gradient of the applied field |
| $\Delta V$ | $(V_f - V_o)$ |
| $\mu$ | Magnetic moment (Bohr magnetons) |
| $M$ | Molecular weight (grams) |
| $P$ | Weight percent of the paramagnetically susceptible solute ions |
| $\Delta W$ | $(W_f - W_o)$ |
| $H$ | Magnetic field intensity |
| $\nabla H$ | Gradient of the applied magnetic field |

All values of μ in Bohr magnetons

| ION SPECIES | REPORTED VALUES FOR μ | μ VALUES COMPUTED HERE |
|---|---|---|
| $Cr^{+3}$ | 3.7 to 3.9 | 3.80 |
| $Fe^{+3}$ | 5.7 to 6.0 | 5.95 |
| $Fe^{+2}$ | 5.0 to 5.6 | 5.50 |
| $Ni^{+2}$ | 2.9 to 3.5 | 3.20 |
| $Cu^{+2}$ | 1.8 to 2.1 | 1.90 |

FIG. 7

| STATED CHEMICAL ASSAY OF Fe IN DRY ORE | EXPERIMENTALLY DETERMINED Fe CONTENT USING FIELD GRADIENT METHOD |
|---|---|
| 69.87% | 69.80% ± 0.20% |
| 69.87% | 69.56% ± 0.30% |
| 69.87% | 69.97% ± 0.25% |
| 69.2% | 69.14% ± 0.26% |
| 69.2% | 69.40% ± 0.30% |

METHOD OF DETECTION OF IONS IN SOLUTION THAT ARE SUSCEPTIBLE TO AN APPLIED FORCE FIELD AND APPARATUS THEREFOR

The invention described herein was made, in part, in the course of or under a contract from the National Science Foundation, an agency of the United States Government.

The present invention relates to methods of and apparatus for determining either the content of an ion in solution or the susceptibility of an ion in solution, said ion being one that is susceptible to an applied force field.

Determination of the content of an ion in solution such as, for example, to find the total iron content in a sample of ore, is a laborious and time-consuming job. Similarly, the determination of the degree of susceptibility of such ion can be difficult, if not impossible.

An object of this invention is to provide a way of determining the content of an ion in solution when that ion is susceptible to an applied force field, and performing this assay with a high degree of accuracy.

Another object is to provide a method of determining the magnetic moment of an ion in solution, as well as obtaining information as to the basic magnetic susceptibility of that solution.

These and still further objects are evident in the description that follows and are particularly delineated in the appended claims.

The objects of the invention are attained by a process that includes, allowing a drop of fluid to fall from a capillary tip with no applied field and recording the volume of that drop (or weight), allowing a second drop to fall from the capillary tip with a gradient field of an applied force field acting at the point of drop formation, said field acting to either levitate the fluid drop or strip it from the capillary depending on the direction of the gradient of that field and the sign of the susceptibility of the fluid, computing the change that has occurred in the drop volume due to the application of the gradient field, and correlating to the volume change that has occurred (or equivalently of the weight change) to the content of the susceptible ion.

The invention is hereinafter described with reference to the accompanying drawing in which.

Colloidal chemists have for many years probed into the properties of liquids by the measurement of such properties as the surface tension. One static method of surface tension measurement, the drop weight method or stalagmometer, provides the starting point for the work that is described here.

Figure 1:
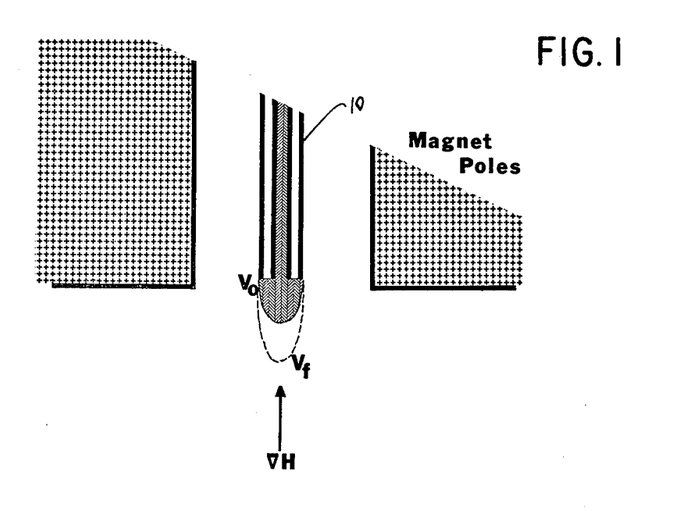
FIG. 1 is a diagrammatic figure showing a capillary tip with a fluid drop, located between the poles of an electromagnet that produces a magnetic field gradient.

The weight of a liquid drop that falls from the end of a capillary tube is directly related to two parameters; namely, the radius $r$ of the capillary and the surface tension $\gamma$. A geometric correction term also arises in the formulation. The gradient field of an applied force now acts vertically along the axis of the capillary tube (e.g., the capillary tube labeled 10 in FIG. 1), so as to maximize the product of the force intensity F and the gradient of the force F at the site of drop formation. (FIG. 1 shows a magnetic field gradient). Under these circumstances, the volume at which the fluid drop falls from the capillary can be altered if the molecules of the solution are susceptible to this applied force.

For example, if the solution exhibits an effective paramagnetic response, a gradient magnetic field increasing up the axis of the capillary as in FIG. 1 will in effect levitate the liquid at the end of the tube and the drop size will increase. If, however, the diamagnetic response of the fluid outweighs the content of paramagnetic ionic species, the drop will be stripped away from the capillary sooner because of the field gradient.

In all of the experimental work done in connection with the present invention, the force employed is magnetic, the ions in solution paramagnetically susceptible and the force due to the applied magnetic field is made to work against gravity. However, if the gradient field of FIG. 1 were made to increase down the axis of the vertically oriented tube 10, rather than up, then the drop would be stripped away earlier than normal if the liquid has an effective paramagnetic response. The Field Gradient Stalagmometer discussed here works equally well for field gradients in either direction along the capillary tube, but a gradient that opposes gravity for a liquid of positive susceptibility is more useful, as will be discussed later.

The emphasis throughout this work is on the use of a magnetic field and field gradient. However, a properly prepared electric gradient field should produce an analogous effect on an electrically susceptible system.

Two of the most apparent uses for this technique are discussed in detail in this disclosure: (1) calculation of the magnetic moments of ions in aqueous solution, and (2) assaying the quantity of a given ion in solution when that ion is paramagnetically susceptible to an applied force field.

In the first use discussed, the Field Gradient Stalagmometer is used for magnetic susceptibility measurements and to obtain information concerning the magnetic moments of ions in solution. Magnetic susceptibility measurements by this method are similar to the accepted techniques of susceptibility determination, such as the Gouy and Quincke methods (Mulay, L. N., *Magnetic Susceptibility*, Interscience Publishers, 1963, pp. 1785–1790).

In the second use discussed, the measurement of the change in drop volume (or drop weight) in the presence of a field gradient provides a quantitative assay of the content of a susceptible molecule. In practice, the drop volume change can be observed to within 0.3% accuracy (typical drop volume is 0.08 ml) without any special concern for temperature changes in the fluid. When the ambient temperature at the site of drop formation is controlled carefully, and a gradient of sufficient intensity is used, the drop volume change is found to be observable to within 0.02 to 0.03 percent. For a typical assay operation, this allows the determination of an ion content to between 0.1 and 0.01 percent accuracy. It should be remarked here that any ion that is susceptible to the gradient field will respond, so that the reading from a mixed system can be very complicated. Some multi-ion systems, however, provide ways of sorting out the various contributions of the components, as is noted later. A discussion of the underlying theory now follows.

Figure 2:
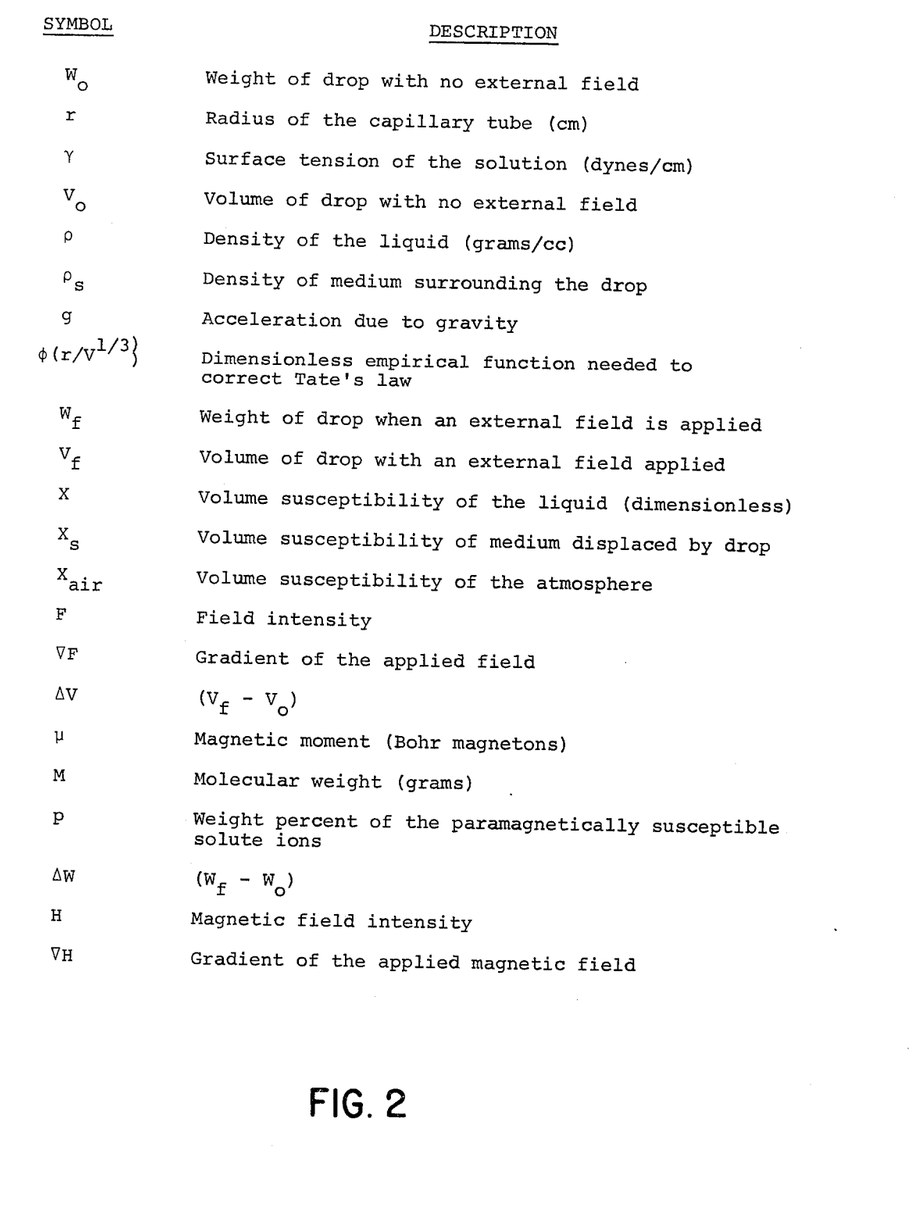
FIG. 2 is a table of all symbols used in the discussion that follows.

One of the simplest methods of surface tension measurement is to determine the weight or volume of a drop that falls slowly from a vertical capillary tube (Adamson, A. W., *Physical Chemistry of Surfaces*, 2nd Edition, Interscience Publishers, New York, 1967, pages 21–24). The theory relating to this process has evolved empirically based upon an overly simplified expression known as Tate's law. In Tate's early formulation of this theory, the actual weight of the liberated drop was given by the relation $$W_o = 2\pi r \gamma$$

where all of the symbols are defined in FIG. 2. An empirical correction has been added to Tate's work, so that the expression becomes $$W_o = g V_o (\rho - \rho_s) = 2\pi r \gamma \phi(r/V_o^{1/3}) \quad (1)$$

The weight $W_o$ used in the above expression (1) is that due to the gravitational and surface tension forces acting on the liquid drop. In the process that is under consideration here, a force in addition to gravity is allowed to act on the system, causing a measurable change in the observed weight and volume of the drop.

Under the influence of the applied force, the new actual weight $W_f$ of the drop at the moment that it detaches is given by the expression $W_f = F$ (Force) $+ F$ (Surface Tension), where the sign of the force is positive if it opposes gravity and negative when it enhances the gravitational force. The surface tension force always opposes the force of gravity. For this development, the gradient field of the applied force is considered to act counter to the gravitational field for a material of positive susceptibility. Therefore, $$W_f = (\rho - \rho_s) V_F g = (X - X_s) V_F (F \nabla F)_{v_F} + 2\pi r \gamma \phi(r/V_F^{1/3}) \quad (2)$$

It has been found for present purposes, the surface tension is not sensitive to the values of the magnetic field used, so the value of $\gamma$ from equation (1) can be substituted into equation (2). Therefore, the expression becomes $$(\rho - \rho_s) V_F g = (X - X_s) V_F (F \nabla F)_{v_F} + (\rho - \rho_s) V_o g \frac{\phi(r/V_F^{1/3})}{\phi(r/V_o^{1/3})} \quad (3)$$

In all of the work that was performed, the medium surrounding the drop was the ambient laboratory atmosphere. However, equation (3) was written to demonstrate the versatility of this method. By forming the drop in various media, the terms $(\rho - \rho_s)$ and $(X - X_s)$ can be varied. For example, for a water drop in an oil medium, the diminishing difference between $\rho$ and $\Sigma_s$ will increase the drop volume, thereby accentuating the effect. The closer the term $(\rho - \rho_s)$ is to zero, however, the more difficult it is to determine the point of detachment of the drop. When $\rho$ is very close to $\rho_s$, a low power field telescope is necessary to observe when the drop releases.

More flexibility is offered by the term $(X - X_s)$. In the magnetic case, for example, when the surrounding medium is normal air, the term $X_s$ is positive because of the presence of paramagnetic atmospheric oxygen. However, if the measurement is done in the presence of another gas which is diamagnetic, this term will be negative and will increase the effect of applying the magnetic field. Due to the low density of gases, however, this susceptibility effect will normally be small.

For work at atmospheric conditions, equation (3) becomes:

$$\rho V_F g = (X - X_{air}) V_F (F \nabla F)_{v_F} + \rho V_o g \frac{\phi(r/V_F^{1/3})}{\phi(r/V_o^{1/3})} \quad (4)$$

Figure 3:
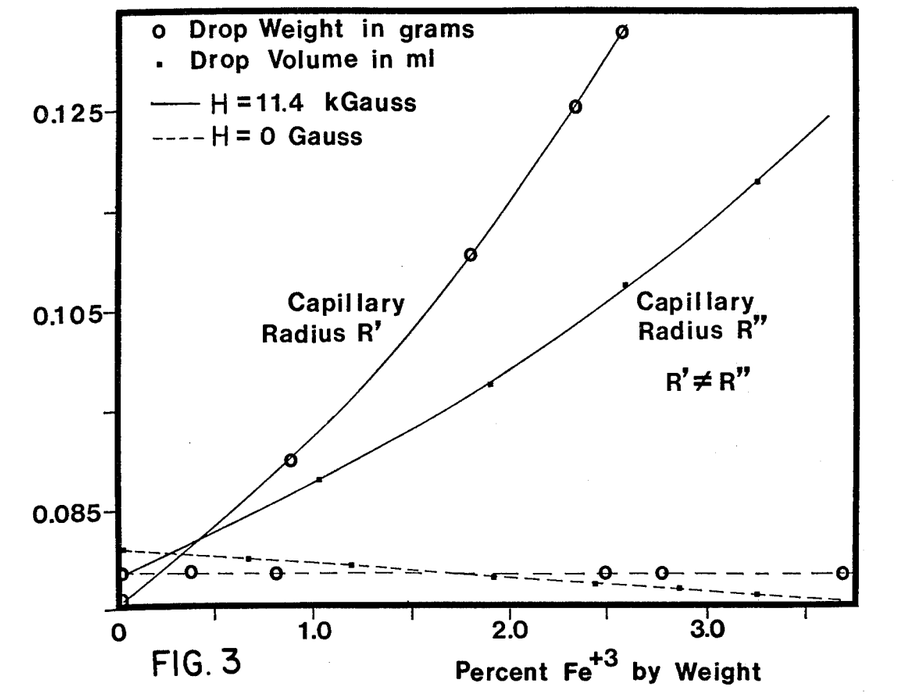
FIG. 3 shows graphically the weight and volume readings that are obtained when the percent weight content of the ion $Fe^{+3}$ is varied in a solution of 15% HCl in water.

FIG. 3 represents readings taken for a system of ferric chloride in a solution of water and hydrochloric acid. As in any of these techniques, care must be taken to know the form that the ion takes when in solution. For example, the effective magnetic moment of an aqueous solution of $Fe^{+3}$ ions is sensitive to the pH and, more importantly, to the species of the ligand ion that complexes to the ferric ion in solution. Work with the salt of ferric chloride is difficult in pure water for anything but very dilute solutions, since the polymerization of the ionic complexes yields results that are difficult to interpret. For this reason, the solvent used was a strong solution of HCl in water.

The data of FIG. 3 show weight and volume readings with and without an applied magnetic field as a function of ferric ion content. These two curves do not represent the same experimental conditions, since the radius of the glass capillary that was used for the weight readings was effectively larger. However, these curves do show the nature of the data that is derived from this technique. The significance of FIG. 3 appears in the readings for no applied magnetic field. The weight readings are constant within the experimental error encountered in the work, whereas the volume readings decrease linearly with increasing iron content, that is with increasing density.

This last fact, which is predicted by equation (1) becomes very significant in the implementation of this technique. For example, when comparing susceptibility measurements between two ionic solutions, the relative densities must also be known. This information is contained in the zero field volume, $V_o$, of the drop since it is inversely related to the solution density. Volume readings, therefore, contain more information than the corresponding weight values.

It is important here to consider how variations that occur between samples affect the determination of the ion weight percent. To illustrate this, consider the readings that are obtained from two samples that contain the same weight percent of a paramagnetically susceptible molecule, but that differ in the content and species of other non-paramagnetic ions. The paramagnetic ions will be referred to as the solute ions.

What is found mathematically is that if the density and surface tension of the two samples are not too drastically different and the species of non-solute ions does not differ magnetically too much from sample to sample, then a computation of the fractional volume change $(\Delta V/V_o)$ gives the ion weight percent to a high degree of accuracy.

Figure 4:
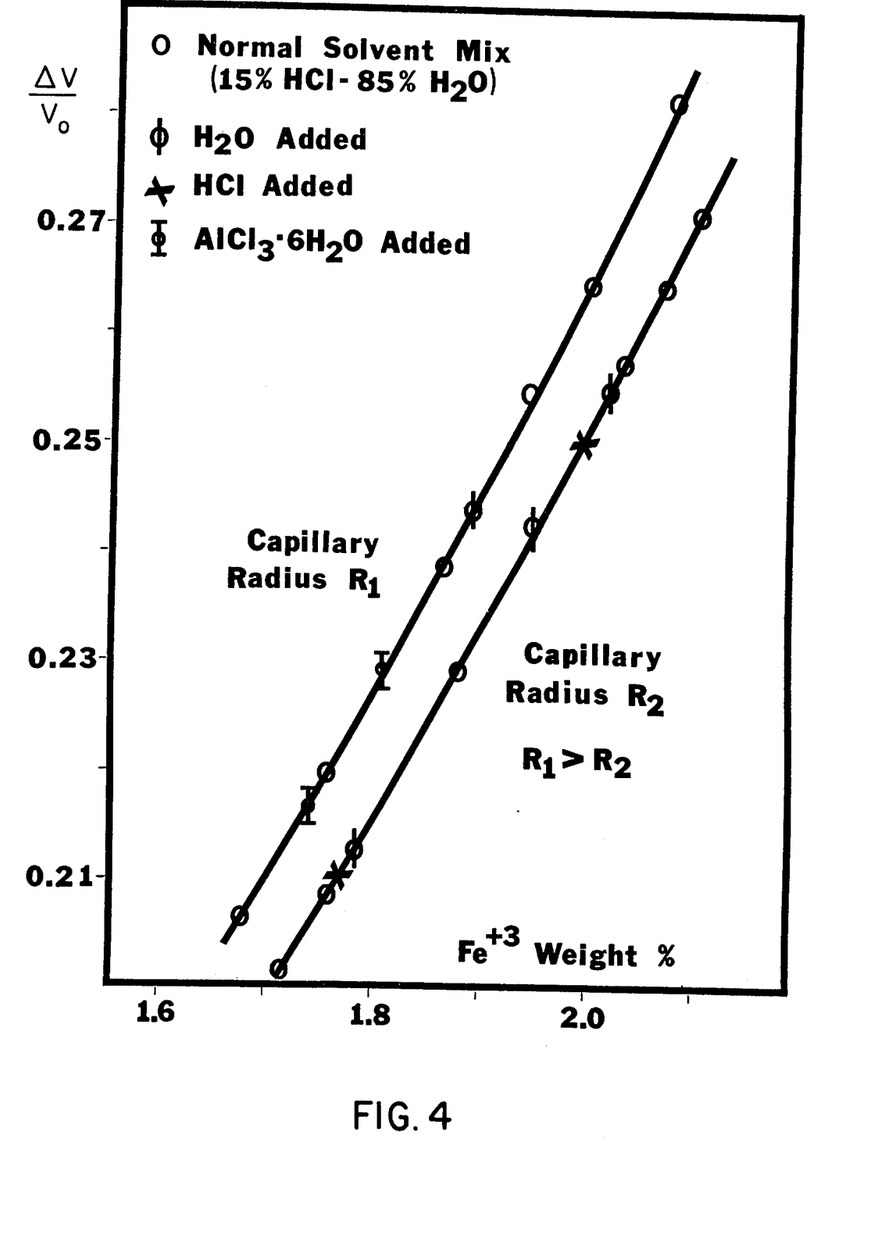
FIG. 4 is a graphical demonstration that the function $\Delta V/V_o$ corrects out the variations that occur due to differing amounts of non-susceptible additives.

FIG. 4 shows experimentally this same point. To a normal mixture of ferric chloride in a prepared solvent (15% HCl in water) were added other ions that change the non-solute nature of the solution. Some of the experimental points were water rich, some acid rich and some contained aluminum chloride as an additive on the order of 2 to 6 percent by weight. When the fractional volume change is plotted against the ion weight percent, as in FIG. 4, the samples with and without additives all follow the same curve accurately.

FIG. 4 plots these points for two different glass capillaries that had slightly different radii. The data of FIG. 4 are presented on a much expanded scale by comparison to the other figures in this disclosure. This figure is the only one on which error bars appear large enough to plot. From FIG. 4, the experimental error is found to be $\pm 0.01\%$ $Fe^{+3}$ by weight.

Figure 5:
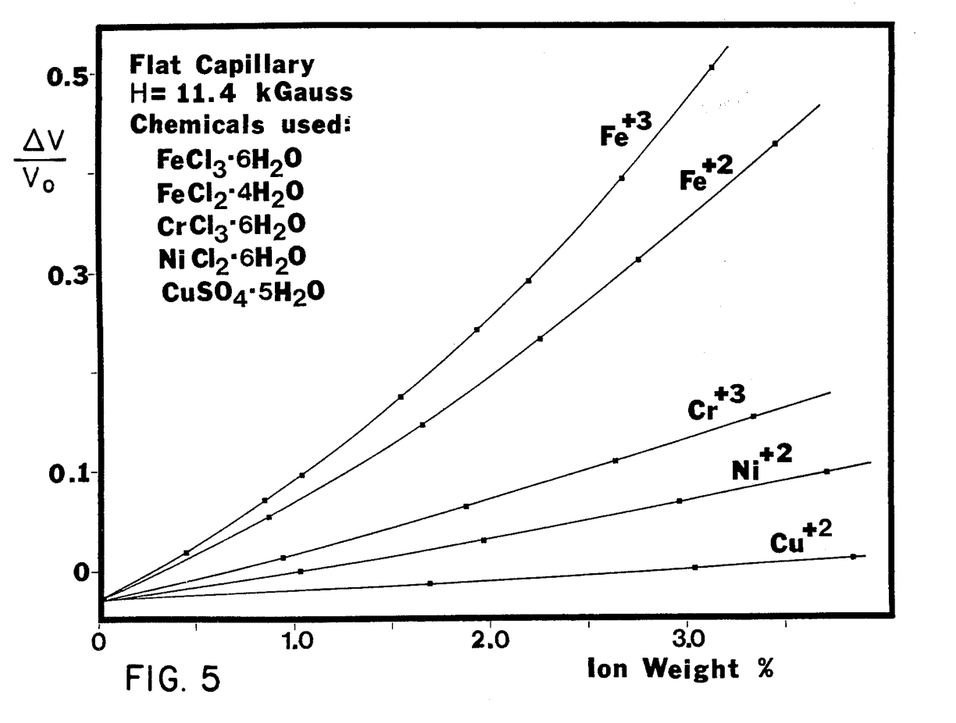
FIG. 5 shows graphically the variations that occur for five different ions in solution.

FIG. 5 gives a plot of $(\Delta V/V_o)$ as a function of ion weight for five different solute ions. The ions that were examined were $Fe^{+3}$, $Fe^{+2}$, $Cr^{+3}$, $Ni^{+2}$ and $Cu^{+2}$. The salts from which these ions were taken are listed on the figure, and the solvent used throughout was a 15% HCl mixture. A flat polished capillary tip was used and the magnetic field strength was 11.4 KGauss.

Using information similar to what is plotted in FIG. 5, it is possible to determine the magnetic moments of paramagnetic ions in solution. The results of the mathematical derivation are described here as they pertain to the present disclosure. From a derivation based on equation (4), an expression can be derived for the ratio of the molar susceptibilities of one ion in solution to a second in an identical solution. This ratio, it is found, depends only on the ratio of the two ion molecular weights (M) and inversely on the ratio of the solution weight percents (p), multiplied by a factor that includes the functions $V_o$, $V_f$, as well as a term that corrects for the underlying diamagnetism of the non-solute molecules in the system. The numerical values of these functions can be obtained from the data of FIGS. 5 and 6.

Figure 6:
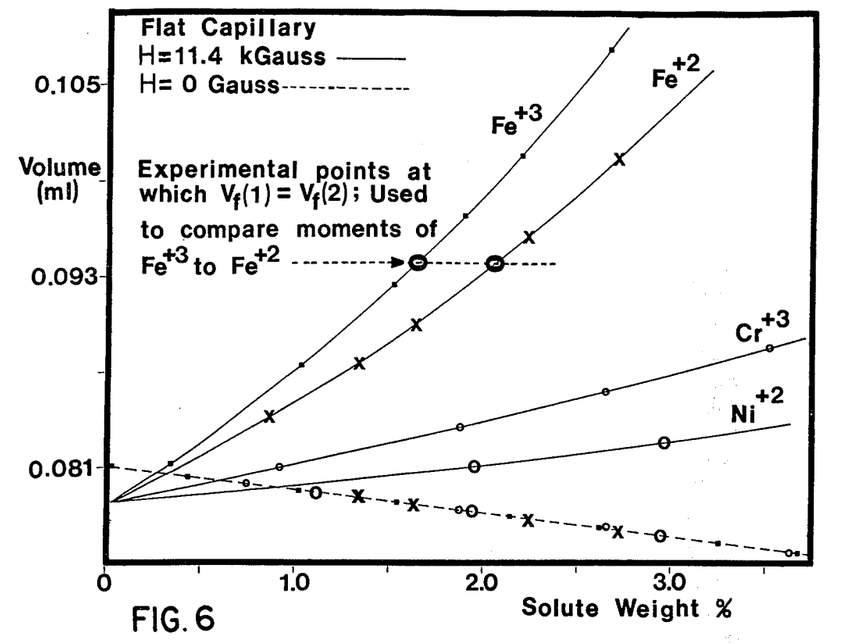
FIG. 6 contains the same information as FIG. 5 with the difference that it is plotted as absolute volume readings rather than percent volume changes.

FIG. 6 is identical to the plot of FIG. 5 except that it shows the absolute volume change rather than $(\Delta V/V_o)$. It is important in computing the magnetic moments to compare the points that have the same $V_f$, since this will eliminate the unknown nature of the term F F over $V_f$. The ratio that is computed for the molar susceptibilities can be used to obtain data on the ratio of the magnetic moments.

Figure 7:
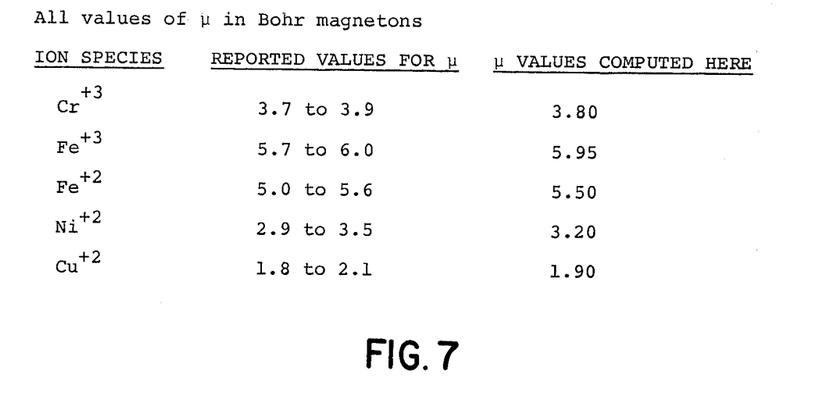
FIG. 7 is a table listing the values of the ionic magnetic moments that are computed using this technique.

It is important to this disclosure, however, to realize that information as in FIG. 5 or FIG. 6 leads to values of the magnetic moment of an ion in solution, as given in FIG. 7. One moment must be known to act as a comparative base for the computation of the others. For this set of computed moments, the moment of $Cr^{+3}$ was assumed to be 3.80, since Selwood gives this number as a near absolute for the moment of $Cr^{+3}$ under widely varying coordination conditions (Selwood, *Magnetochemistry*, Interscience Publishers, 1956, page 204). Based on this number, the other moments that are calculated are very close to what is expected.

As discussed earlier, the function $(\Delta V/V_o)$ will correct for minor variations in the density, surface tension and diamagnetic response of the solvent molecules. This was experimentally demonstrated, as indicated by FIG. 4. This is a very important fact, since it allows the determination of the weight % of the solute ion content with reasonable assurance that this calculation is not sensitive to the variations that can and do occur between samples. For example, this technique can be used to determine the total iron content in a sample of an iron ore that has been digested in a solution of HCl and water, even though the ore samples can vary in the content of silicas and clays and other non-solute additives. As long as two samples of the ore are not dramatically different, a quantitative assay can be made.

The advantage of such a method of total iron analysis is the ease, speed and accuracy with which the assay can be performed. The fluid in the Field Gradient Stalagmometer apparatus is in contact with rubber and glass only, so that a strong solution of HCl can be used. Therefore, the ore sample can be digested in warm HCl and diluted to a 15% acid solution, so that the calibration curve of FIG. 5 can be used. With two or perhaps three readings (approximately 10 to 20 minutes) and with the suitable calibration curve, the total Fe content can be determined accurately. This stands in sharp contrast to existing methods of chemical analysis for total iron content.

The present approach has obvious value when dealing with a single component system (only one species of solute material) in which the content of the solute ion must be accurately determined, as in FIGS. 5 and 6. Also, a system in which the content of solute ions remains constant but the magnetic response of the system changes (for example, due to the polymerization of the ions) is easily monitored using this technique. This Field Gradient Stalagmometer has potential use as a very simple research tool.

The only serious drawback that occurs when using this technique for quantitative assay is when dealing with a system that has more than one species of paramagnetically susceptible ion. When there are two kinds of solute ions present, each ion contributes to $(\Delta V/V_o)$ in proportion to the square of its magnetic moment. Therefore, such a two-component system requires two data points in order to solve for the two unknowns. This is possible in many circumstances, due to the different oxidation states of the ions involved. An example that relates to iron ore analysis is considered now.

The statement was made earlier that iron analysis can be performed on an iron ore sample quickly and accurately. Now it is of interest to consider what effect, if any, the different oxidation states of iron will have on this analysis. When an unknown sample of iron ore is dissolved in a strong acid such as, for example, HCl, the solution will contain some ratio of $Fe^{+2}$ to $Fe^{+3}$ ions, which is exactly the ratio that existed in the ore. The use of HCl as a solvent under normal conditions of low oxidation potential prevents oxidation of the ferrous species to the ferric form. With a minimum of two readings on the Field Gradient Stalagmometer, it is possible to determine both the total iron content of the system, as well as the $Fe^{+2}/Fe^{+3}$ ratio.

To show this, reference will be made to the graph of FIG. 8. In this graph, a section of the calibration curve for $Fe^{+2}$ and $Fe^{+3}$ is shown. The points on this graph that are numbered 1 and 4 are the same sample at different ratios of $Fe^{+2}$ to $Fe^{+3}$. These variations are caused by oxidation of the ferrous to ferric form using hydrogen peroxide $H_2O_2$. As the oxidation of $Fe^{+2}$ to $Fe^{+3}$ becomes more complete, the experimental readings fall on a straight line that approaches the $Fe^{+3}$ calibration curve. When all the ferrous ions have been oxidized to the ferric form, the readings begin to move down the $Fe^{+3}$ curve (point 4) because the addition of the $H_2O_2$ only decreases the weight percent of the iron ions.

Figure 8:
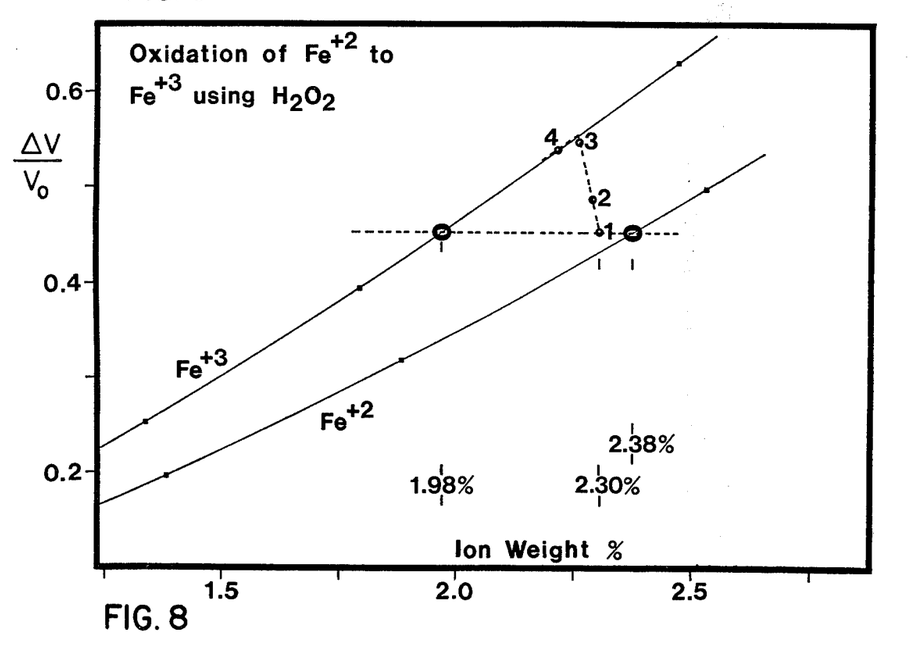
FIG. 8 shows graphically the oxidation of the ferrous ion to the ferric form in solution, as demonstrated by this process.

Each of the points 1, 2 and 3 in FIG. 8 correspond to well defined ratios of ferrous to ferric ions, which can be easily determined. Point 4 has a unique position on the $H^3$ calibration curve, since an excess of $h_2O_2$ has assured that all of the ferrous ions have been oxidized. The relative position of point 4 to the other three points is given absolutely, since the weight % of $H_2O_2$ needed to go from points 1, 2 or 3 to point 4 is known. Therefore, when performing an analysis on the sample represented by point 1, the only data points that are absolutely necessary are points 1 and 4. Care must be taken to ascertain the weight % of $H_2O_2$ added to go from point 1 to point 4. Given an unknown sample like that represented by point 1, then, it is necessary only to take two data points to obtain the total iron content in weight percent and the ferrous to ferric ratio. The ferrous to ferric ratio gives a good qualitative indication as to the ratio of magnetite to hematite in the original ore that was digested in acid, when iron ore is being analyzed. These two facts concerning the unknown sample take the order of 15 to 30 minutes to obtain.

Figure 9:
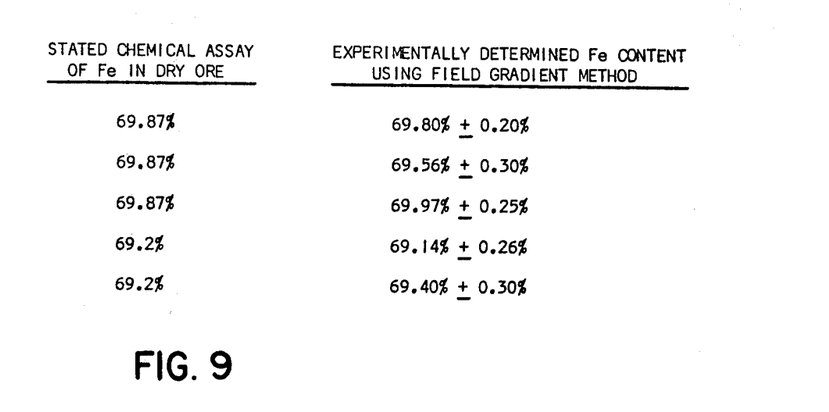
FIG. 9 is a table showing the experimentally determined values of the total iron content for some laboratory samples of an iron ore.

FIG. 9 presents results that were obtained when iron oxides of known content were analyzed. In each case, the time that was required for a single reading was no more than 15 minutes, starting from the already digested ore. A calibration curve for $Fe^{+3}$ was used, as for example the curve included in FIG. 5 or 6 The use of HCl as a solvent was chosen to expedite the subsequent iron ore analysis.

Two methods have been used in this work for the determination of the drop size change that occurs when a magnetic field is applied. A simple measurement of the drop weight was first used to establish the basic features of this effect. This technique was then abandoned in favor of the more versatile approach of measuring the change in the drop volume. This latter method is more useful because of the simplicity of the apparatus involved as well as the comparative ease and greater accuracy with which individual measurements can be made. The apparatus employed is discussed hereinafter with reference to FIG. 17.

The specifics of the experimental procedure that was followed in the measurement of drop weight and volume are preceded by some general comments. To obtain the limits of accuracy that are reported here, it is important to allow the last 1 to 2 percent of the drop volume to flow into the capillary slowly (Adam, N. K., *The Physics and Chemistry Surfaces*, Dover Publications, 1968, page 329). This will allow the breakaway of the drop from the end of the capillary to be clean and even. If such care is taken, for example, the drop volume can be measured reproducibly to an average deviation of 3 parts in 10,000, or 0.03 percent accuracy. Since the majority of the drop volume can be fed to the tip rapidly without affecting the measurement, it is possible to make a single drop volume reading in a minute or less.

Figure 10:
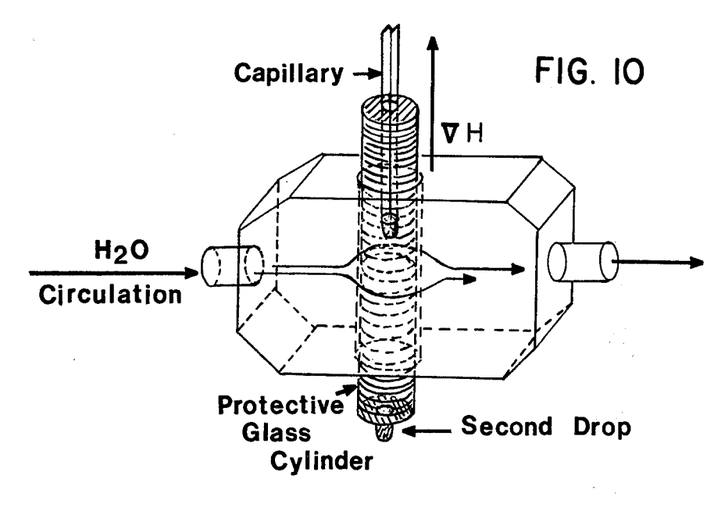
FIG. 10 is a diagrammatic figure that shows the placement of the capillary tube in a temperature-controlled environment.

If the accuracy of 0.03 percent is required, it is necessary to control the ambient environment at the point of drop formation. This was accomplished in this work using a temperature controlled water bath that circulated around a cylindrical glass tube. This glass tube enclosed the region of the drop formation. (See FIG. 10.) The temperature of the bath was controlled to within 0.2°C. The base of the glass cylinder that surrounded the capillary tube was stopped down to a small circular aperture, so that it would retain in a second hanging drop the liquid that had fallen from the capillary tube. This serves a dual purpose. First, it provides a barrier against air currents that might otherwise circulate through the inside of the glass cylinder and destabilize the capillary drop. Second, the presence of the fluid at the base of the glass cylinder helps to saturate the atmosphere in the tube so that evaporation loss from the surface of the drop as it forms is minimal.

If the accuracy in the volume readings of 0.3 percent is satisfactory, then the temperature control is not necessary. In this case, a simple cylindrical glass tube should surround the capillary tip so that air currents do not detach the drop prematurely. A drop of liquid should be made to hang from the bottom of the glass tubing as before.

The end of the capillary tube from which the drop falls should be either hand polished or fire polished to remove scratches from the surface. If imperfections in the surface remain, there is an inaccuracy in the value of the radius r that is used in computations but this error occurs consistently and does not affect the accuracy of the results. More importantly, however, these surface scratches make it difficult to remove all surface dirt and grease prior to a series of readings. Dirt, and especially grease, on the capillary tip will introduce a variable error which diminishes the accuracy of the results. The glass capillary tip should be cleansed by allowing a strong solution (15 percent) of hydrochloric acid to drip from the end of the capillary before starting a series of readings. For most of the work presented here, a flat fire-polished pyrex glass capillary was used. The diameter of this tube measured approximately 6.4mm.

Figure 17:
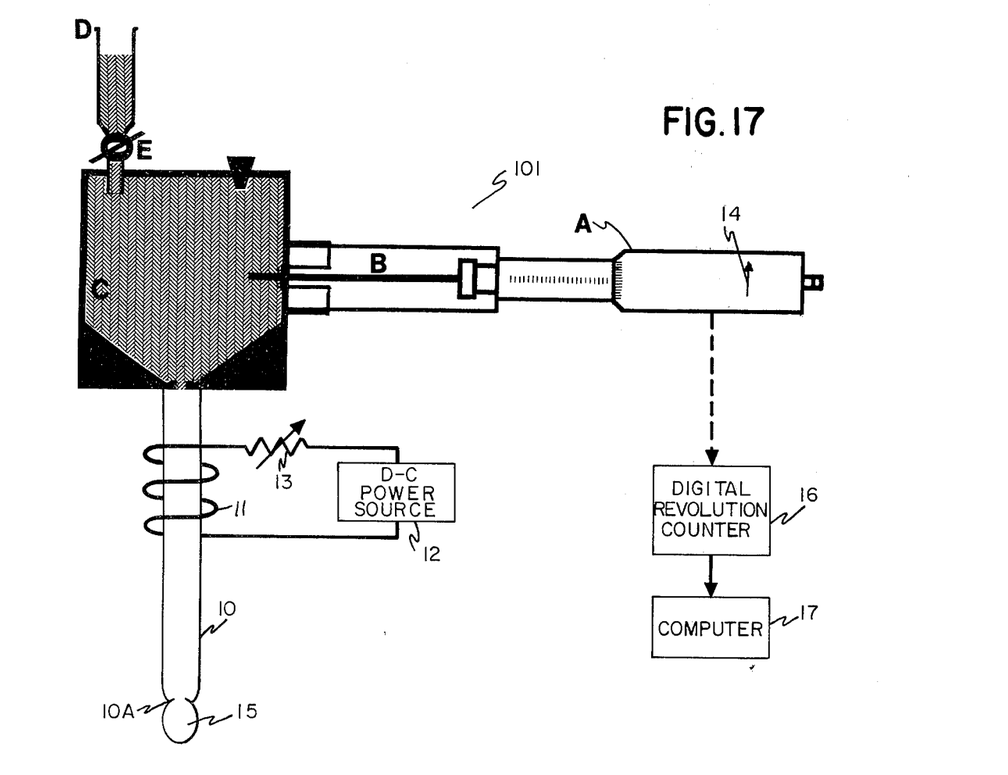
FIG. 17 is a diagrammatic representation of apparatus adapted to determine the fractional content in a solution of an ion susceptible to a magnetic field.

For the volume measurements during drop formation, a fifty turn precision micrometer A in FIG. 17, (50 turns to an inch) with a 0.25 ml precision ground glass plunger B was mounted on the side of a 10 ml reservoir C. The precision micrometer with the 0.25 ml plunger barrel reads the drop volume to within $10^{-5}$ ml, with a reproducibility of $3 \times 10^{-5}$ ml. The glass plunger B had access to the reservoir through an o-ring seal. Valved ports allowed easy filling and cleaning of the reservoir, and a second smaller reservoir D was attached above the main one and separated from it by a teflon stopcock E.

When making a volume measurement, the reservoir C was filled with liquid, care being taken to exclude air bubbles. The valve E separating the smaller container from the larger one was now opened to allow some liquid to flow from the end of the capillary 10. In this way, air was flushed from the capillary tube 10 as well as from the liquid at the capillary tube tip. Before isolating the main reservoir, 80 to 90 percent of a drop volume was allowed to form on the capillary tip. With the reservoir sealed, the micrometer was manually advanced rapidly at first and very slowly toward the end, until the drop on the capillary detached. The reading of the micrometer was recorded. Then the micrometer was advanced again until a second drop fell from the tube end. The difference in these two readings represented the drop volume.

Use of a micrometer in this manner allows great accuracy since the positive displacement of the fluid by the glass plunger makes it easy to feed the last 1 to 2 percent of the drop volume slowly. This procedure was unaltered in the presence of the magnetic field.

Weight measurements also utilized the slow feed capability of the micrometer system. The capillary drop was allowed to fall into a weighing bottle whose weight had been recorded on a four place Mettler balance. The new weight of the bottle then gave the drop weight. The Mettler electrobalance measures to within one ten-thousandths of a gram. Including inaccuracies introduced by evaporation of the drop from the weighing bottle, handling of the bottle and zero drift of the balance, the overall reproducibility of the drop weight was $3 \times 10^{-4}$ grams, which is less accurate than the volume readings.

The equipment required for the volume measurement is much simpler and cheaper than that for a weight measurement. A volume measurement also gives more information than a weight reading, since $V_o$ is related to the fluid density. All of these reasons make a volume measurement superior to a weight reading.

Some remarks should be made concerning the intensity of the magnetic field and the magnetic field gradient that was used in the work herein discussed, as well as the effect of changing the intensity of the magnetic field.

Figure 11:
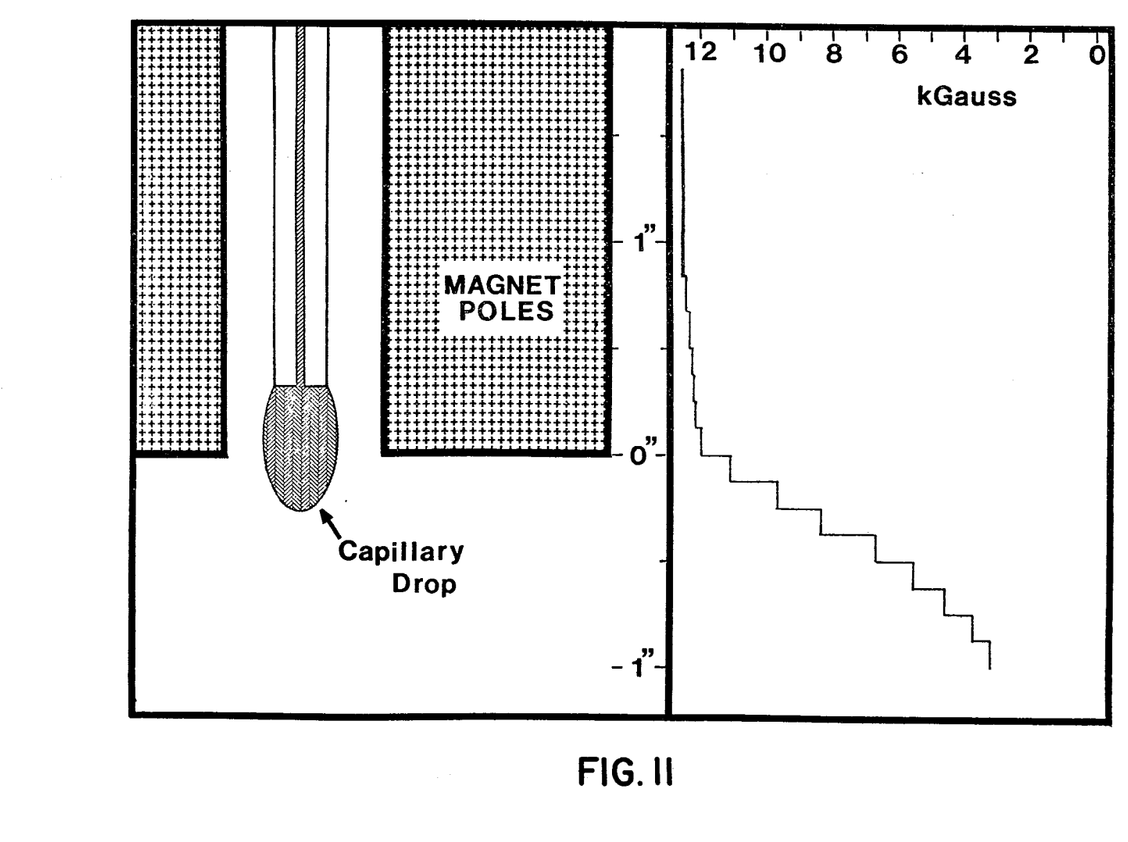
FIG. 11 shows diagrammatically the placement of the capillary tube between the magnetic poles, as well as a plot of the magnetic field gradient that was used in this work.

FIG. 11 shows schematically the magnetic field gradient used in most of the work described here. The intensity of the magnetic field for these gradient readings was 12.5 kGauss in the homogeneous region. Before data was taken in this work, the point of maximum volume $V_f$ was determined by trial and error. That point is pictured in FIG. 11 by the drawing on the left-hand side of the graph. From the gradient numbers in this graph, it is clear that the optimum placement of the capillary tube does not put the liquid drop in the region of highest gradient. However, the force due to the magnetic field depends on the product of the magnetic field intensity and the gradient of that field over the volume of the drop, which is maximum for the position of the capillary tube.

Figure 12:
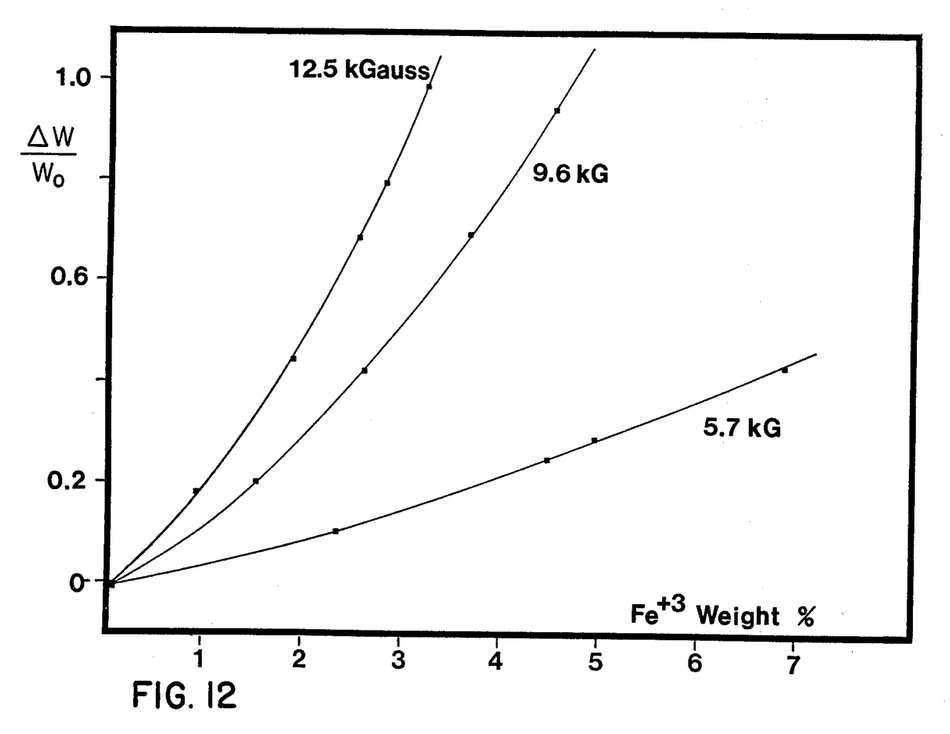
FIG. 12 shows graphically the change in drop weight (equivalent to plotting the change in drop volume) that occurs for different settings of the magnetic field strength.

FIG. 12 indicates the effect of altering the magnetic field intensity. The larger the percent volume change that occurs, the more accurate is the determination of the solute ion weight percent. Therefore, lower magnetic fields can be used, as is shown in FIG. 12, but at these lower field values, the same change in the ordinate values causes a larger change in the abscissa numbers. The experimental accuracy, in other words, decreases for decreasing field strengths.

The data that has been presented here in accurate and reproducible because it is not necessary for the gradient to be constant over the drop volume. What is important is that the magnetic field contour remain unchanged for the same set of experimental conditions. If a drop of a given volume $V_f$ always experiences the same variation of the term F F over its volume, then the readings will be consistent and reproducible. This requires that the magnetic field intensity be accurately adjusted and that the capillary tube remain at the same physical location in the magnetic contour. Under those circumstances, the functional relationship between $\Delta V/V_o$ and the ion weight percent will not be predictable (because the gradient of the magnetic field is not constant over $V_f$) but it will be reproducible.

Figure 13:
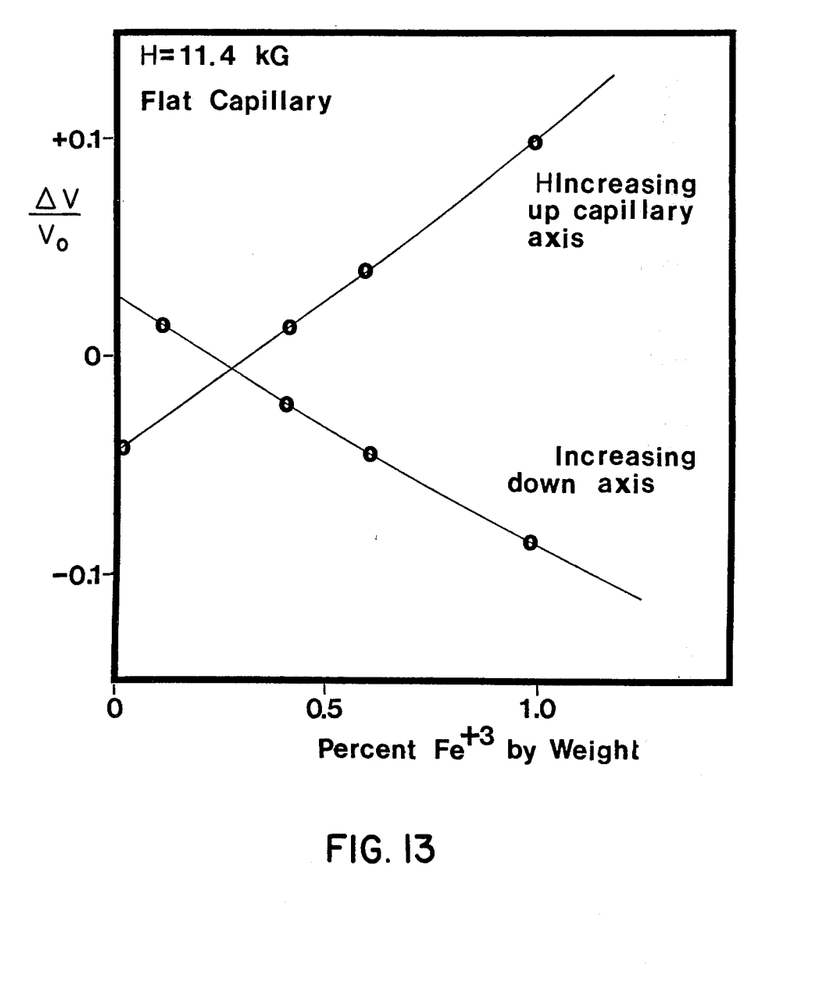
FIG. 13 shows graphically the curves that are obtained when the gradient direction acts up and down the capillary axis.

For the work that has been described thus far, the magnetic field gradient increased up the capillary axis. For a fluid with an effective paramagnetic response, this has the effect of levitating the capillary drop. It is also possible to have the gradient increase down the axis. Such a force will add to gravity for a fluid of positive susceptibility and strip it from the capillary earlier. The magnet that was used in this work has cylindrical iron poles with a base diameter of 4 inches. Placement of the capillary tube as shown in FIG. 11 takes advantage of the gradient that increases up the axis. By placing the capillary above the poles rather than below as in FIG. 11, the gradient magnetic field is made to increase down the axis. FIG. 13 presents data for the percent volume change using both gradient directions.

When the force works against gravity to levitate the liquid at the capillary tip, it is often possible to obtain $(\Delta V/V_o)$ values greater than unity, or equivalently values of $V_f$ more than double the zero field value of $V_o$. For example, using a conical capillary a $(\Delta V/V_o)$ value of 1.0 occurs for 3.1% $Fe^{+3}$ content, and values for $(\Delta V/V_o)$ as high as 1.4 were observed for higher $Fe^{+3}$ contents. When the applied field works with gravity, it is not possible to obtain accurate readings for values of $(\Delta V/V_o)$ greater than about $-0.9$. Therefore, using the field gradient to levitate the fluid is more useful and more accurate.

Figure 14:
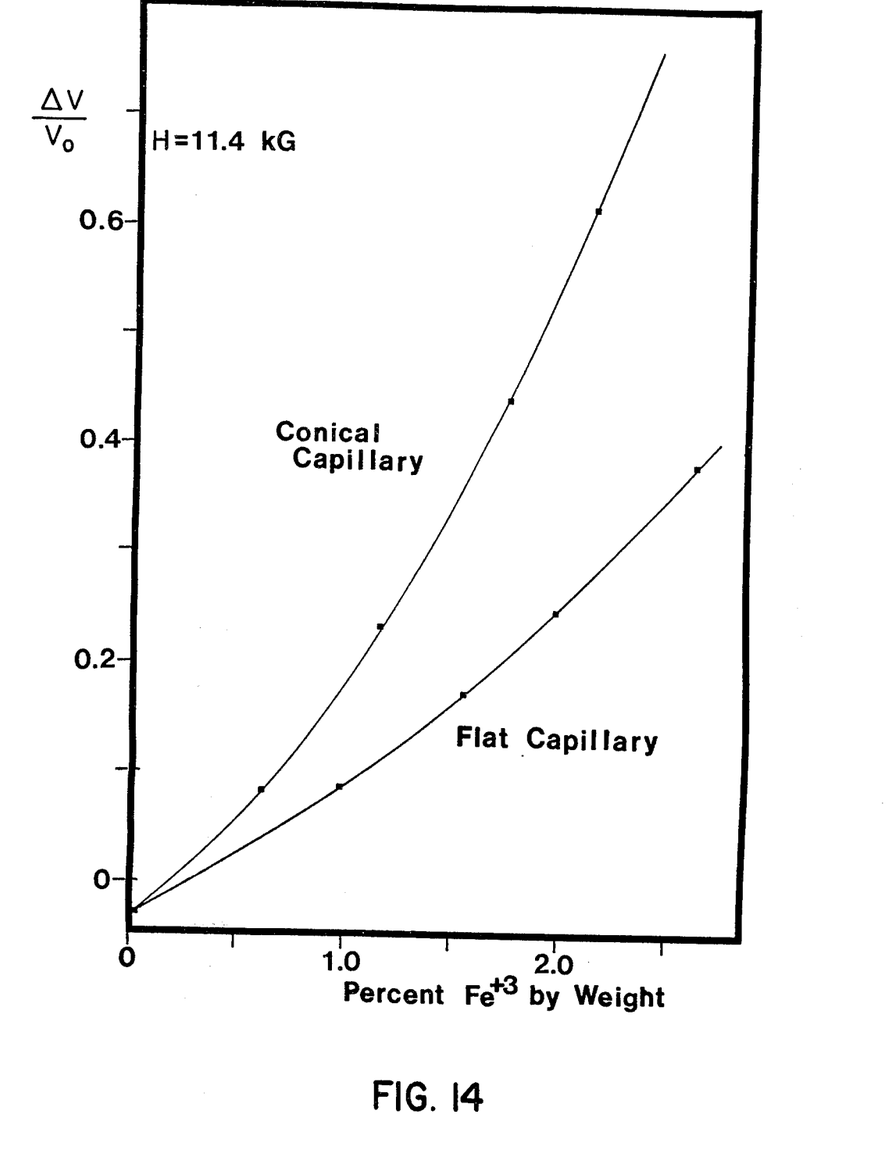
FIG. 14 shows graphically the significantly larger effect that is obtained when using a capillary tip with a conical geometry.

It is possible to increase the $(\Delta V/V_o)$ change that occurs by altering the contour of the capillary tip. FIG. 14 shows a comparison between two capillary geometries. A flat polished capillary tip is used most often in measurements of surface tension by the drop weight technique, and it was used in most of the work discussed thus far. However, it is found experimentally in FIG. 14 that a cone-shaped tip increases the change in $(\Delta V/V_o)$ by more than a factor of two. This will in turn improve the accuracy of the experimental results, because a steeper slope for the FIG. 14 curves means greater accuracy in the determination of the ion weight percent.

Figure 15:
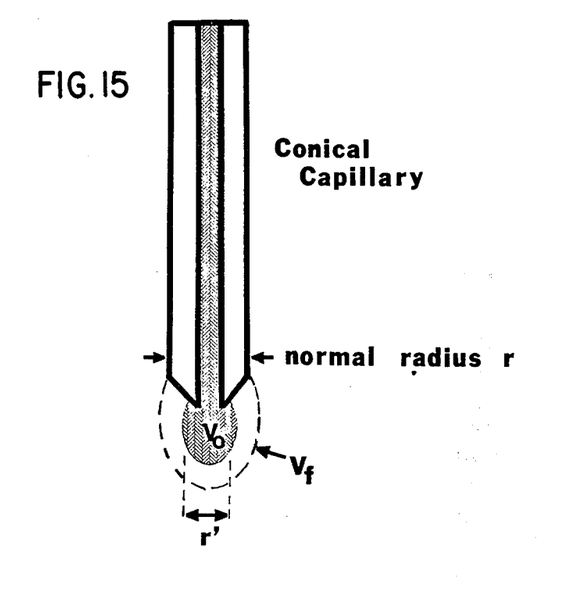
FIG. 15 is a schematic representation of a conical tip geometry.

FIG. 15 is a sketch of a conical capillary tube. At zero magnetic field, as the drop volume increases, the drop moves down the cone and reaches a value of the effective capillary radius $r'$ that is smaller than the radius of the capillary r. When the magnetic field is applied, however, the levitating force due to the field allows the drop to remain at the top of the cone and so the effective radius is closer to $r$ than to $r'$. This, in effect, decreases the value of $V_o$ that is observed, while it does not alter significantly the volume $V_f$. The net result is that $(\Delta V/V_o)$ increases dramatically. Although the radius is variable in the manner just discussed, the reproducibility and accuracy is not altered. Other tip geometries might also enhance this effect. Because of the contact angle between the fluid and the tip, a hemispherical capillary tip would probably be even better than the conical tip already discussed.

The radius of the flat capillary that was used in this work is $r = 6.4$mm. For a typical conical capillary tip, the value of $r = 6.4$mm and $r'$ would measure approximately 2mm. The selection of these values was arbitrary, and it is possible to enhance this effect still further by increasing the value of $r$ more. The literature on surface tension measurements is replete with discussions concerning the optimum value of the radius $r$, and values greater than 6.4mm are common. (See Campbell, "Surface Tension Measurement by Drop Weight Technique," J. Phs. D. Appl. Phys., 1970, Vol. 3, pages 1499–1500.)

The capillary itself can be used as a conductor of magnetic flux, producing a magnetic gradient at the capillary tip. For example, if the capillary tube designated 10 in FIG. 1 is made of a magnetically permeable material like iron and a coil is placed around that capillary tube, as shown in FIG. 17, then flux lines are conducted through the tube itself and they diverge from the capillary tip. This creates a gradient field at the end of the capillary tube, producing the effect that is discussed herein.

The magnetic syringe greatly simplifies the practical considerations that are involved in making a proper magnetic geometry. If corrosive fluids are to be used in this process, the iron tube requires coating to prevent degradation. Also, sufficient current is required in the coil arrangement so that the magnetic field intensity as well as the gradient are of ample strength. However, this approach has the advantage that the magnetic gradient is completely defined by the chosen geometry of the capillary tip. Therefore the relationship between $(\Delta V/V_o)$ and the ion weight percent would be easier to predict, although reproducibility would not be any different than the magnetic geometry already discussed in this work.

In the foregoing, a magnetic force field was used to demonstrate the usefulness of the Field Gradient Stalagmometer. A properly prepared electric gradient should act similarly on a fluid that contains electrically susceptible molecules. There are, however, significant differences between the magnetic and the electric case that makes the electric gradient method less useful.

When an ion with a magnetic moment is added to a solution, that ion produces a magnetic effect that is roughly 100 times or more greater than the magnetic strength of the solvent ion that it replaces. Therefore, at even low concentrations of magnetically susceptible ions, it is possible to observe changes that occur. However, in the case of an electric field, the replacement of one ion in solution by another goes almost unnoticed since electric dipole moments in solution vary only slightly from one molecular species to another. Therefore, in the electric case, only large solute contents are detectable, but with such solutions significant changes in the surface tension and density of the fluid are also occurring. This makes the results difficult to interpret.

Figure 16:
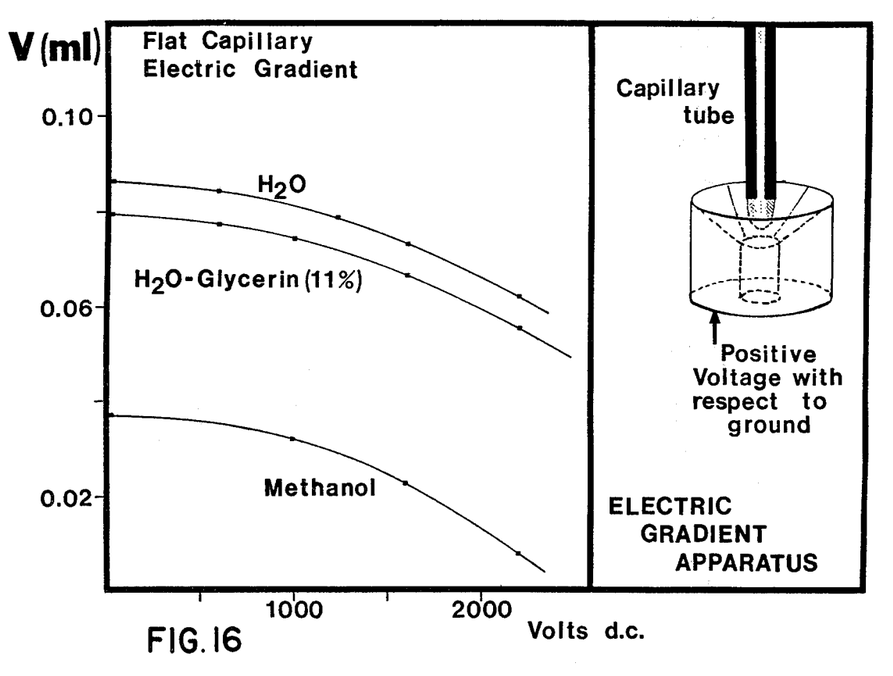
FIG. 16 shows diagrammatically the apparatus used for the case of an electric force field, as well as the volume change that can be observed for three different fluid systems.

Further, it is more difficult to structure an electric gradient. In creating an electric gradient, it is far easier to let the gradient act down the capillary axis, as depicted in FIG. 16. A piece of brass was machined to produce a cone-shaped cavity. This brass electrode was connected to the high side of a regulated d.c. power supply, which created a downward acting gradient and increased the force that would strip the fluid from the capillary. FIG. 16 also shows the volume change that occurs as a function of voltage for pure water, water-glycerin and methanol systems. The values for the water-glycerin system are below that of pure water, since the addition of the glycerin increases the density and therefore decreases the observed volume $V_o$. Methanol is a fluid with a very low surface tension, and the volume readings demonstrate this.

Keeping the foregoing principles in mind, reference is again made to FIG. 17 that shows diagrammatically apparatus or system 101 that is adapted to determine the fractional content in a solution of an ion susceptible to a magnetic field. The system 101 contains the reservoir or chamber C to receive the solution from the reservoir D through the valve E. The elevated source D assures that the chamber C is completely filled and, when filled, the valve E is closed, at this juncture the chamber C is sealed, as before noted. The capillary tube again designated 10 in FIG. 17 is made of a magnetically permeable material so that when a coil 11 is energized by a d.c. power source 12 it magnetizes the tube 10 in the axial direction causing fringing fields to exist at the tip labeled 10A of the tube 10. The magnitude of the field in the tube 10 and, therefore, the magnitude of the fringing fields at its tip, is controlled by a variable resistance 13. The plunger B when moved to the left in the figure by rotating the micrometer A in the direction of the arrow numbered 14, feeds the solution in the sealed chamber C slowly so that a drop 15 will form at the capillary tip 10A, as shown. As the drop size is increased by slowly moving the plunger B to the left, the drop will eventually attain a size sufficient to cause it to separate from the tube. The size of the drop thus emitted can be determined by noting the difference in the reading of the micrometer A between initiation of the drop and the instant when the drop separates from the tube tip. In fact, what is done is to take the reading at the time of the last drop, making it the initial reading for the next drop. In this way, the size (in this case the volume) is determined and, of course, it is determined without a magnetic field (i.e., $V_o$) and with a magnetic field (i.e., $V_f$), as before discussed. In the work done and above referred to, the operation has been manual and the correlation function was accomplished by reference to graphs, as above explained. The micrometer readings can, however, be sensed by a digital revolution counter 16 and the readings can be fed to a general or special-purpose computer 17 to give the fractional ion content in the drop on the basis of $V_o$ and $V_f$. It is not particularly difficult to program a general purpose computer to perform the necessary functions. For magnetic ions the tube 10 is made of a soft permeable material so that its magnetization drops substantially to zero when the background field is removed. It will be appreciated, however, on the basis of the above explanation, that what is required here is two levels of magnetic field, and it is not necessary that one be zero, or substantially so, but as a practical matter it is desirably so. Also, the high field can be one which saturates the tube 10; again this is not necessary, but accuracy of the ion determination is enhanced.

Since the electric case is sensitive mainly to the solvent and not to ions in that solvent, an electric gradient could be used to meter out a set volume of solution from a capillary of a set radius. By changing the magnitude of the applied electric field, the volume of the capillary drop would also change, as shown in FIG. 16.

Further modifications of the invention herein disclosed will occur to persons skilled in the art, and all such modifications are deemed to be within the spirit and scope of the invention as defined by the appended claims.

What is claimed is:

1. A method of determining the fractional content in a liquid solution of an ion susceptible to a gradient field of an applied force field, that comprises, forming at the end of a capillary tube a first drop of the solution containing the ion with no applied gradient field and noting at least one of the volume, $V_o$, and equivalently the weight, $W_o$, of the first drop that detaches from the capillary tube, forming at the end of the capillary tube a second drop of the solution containing the ion with a gradient field of an applied force field in the region occupied by the second drop and noting at least one of the volume, $V_f$, and equivalently the weight, $W_f$, of the second drop that detaches from the capillary tube in the presence of the gradient field, determining at least one of the volume change, $\Delta V$, between the first and second drop and the actual weight change, $\Delta W$, therebetween, and correlating at least one of the volume change, $\Delta V$, and the actual weight change, $\Delta W$, with the content in the drops of the susceptible ion.

2. A method as in claim 1 in which the end of the capillary tip is disposed in a fluid medium.

3. A method as in claim 2 in which the density of the medium surrounding the capillary drop is varied to alter the effective density of the forming drop.

4. A method as in claim 2 in which the susceptibility of the medium surrounding the capillary drop is changed to alter the effective susceptibility of the forming drop.

5. A method as in claim 1 in which the applied field gradient is a magnetic field gradient.

6. A method as in claim 5 in which the susceptible ion is an ion from a class of ions that have a positive magnetic moment in solution.

7. A method as in claim 1 in which the applied field gradient is an electric field gradient.

8. A method as in claim 1 in which the capillary tube is vertically oriented and in which the gradient increases up the capillary axis and acts to increase the drop weight for a fluid of positive susceptibility to the applied field.

9. A method as in claim 1 in which the capillary tube is substantially vertically oriented and in which the gradient decreases up the capillary axis and acts to decrease the drop weight for a fluid of positive susceptibility to the gradient field of the applied force field.

10. A method as in claim 1 that utilizes the correlation between volume change or the weight change and susceptible ion content to determine the content of a susceptible ion in an unknown sample.

11. A method as in claim 10 in which the force field is a magnetic gradient force field and the susceptible ion is the ferric ion ($Fe^{+3}$), said method being used for determination of the total iron content of the solution.

12. A method as in claim 10 that uses a magnetic field gradient and a mixture of the ferric and ferrous species in solution, said solution containing a strong acid at a low oxidation potential to maintain the integrity of the iron oxidation states.

13. A method as in claim 12 in which the method of claim 1 is first applied to the mixture of ferric and ferrous species and then an oxidant is used to convert the ferrous species to the ferric species, thus allowing the determination of the total iron content as well as the amount of the original sample that was the ferrous species.

14. A method as in claim 1 that utilizes the correlation between volume change or weight change and susceptible ion content to compare magnetic moment values for the ions in solution, such comparison giving the value of the magnetic moment of one ion when the magnetic moment value of the other ion is known.

15. A method as in claim 1 in which any liquid solution can be used.

16. A method as in claim 1 in which the temperature at the site of drop formation is controlled carefully to within a few tenths of a degree Centigrade so as to increase the accuracy of the drop volume or weight determination.

17. Apparatus for determining the fractional content in a liquid solution of an ion positively susceptible to a magnetic field, that comprises, a capillary tube made of a magnetically permeable material, means for magnetizing said capillary tube in the axial direction, means for feeding the solution into the capillary tube slowly so that drops will form consistently at the capillary tip, the volume and weight of the drops being different for a condition wherein the capillary tube is magnetized than for a condition wherein the capillary tube is not magnetized, and means for determining at least one of the volume and weight of emitted drops with and without a magnetic field applied to the capillary tube and for determining the difference in at least one of the volume and the weight of the emitted drops with and without a magnetic field applied.

18. Apparatus as claimed in claim 17 in which the volume only of the drops is determined with and without a magnetic field applied to the capillary tube and in which the means for feeding the solution determines, as well, the volume of the drop in each instance.

19. Apparatus as claimed in claim 18 in which the means for introducing the solution to the tube and for determining the drop volume comprises a micrometer.

20. Apparatus for determining the fractional content in a liquid solution of an ion susceptible to a magnetic field, as well as the degree of susceptibility of the ion, that comprises, a capillary tube made of a magnetically permeable material, means for applying a magnetic field to the capillary tube to magnetize the same, means for feeding the solution into the tube slowly so that a drop will form at the capillary tube tip and separate therefrom, the size of the drop being variable as a function of the susceptibility of the contained ion, the content of the ion in the solution and the magnetization of the capillary tube, and means for determining the size of a drop of the solution emitted from the capillary tip at one value of magnetization and the size of a drop of the solution emitted from the capillary tube tip at another value of magnetization.

21. Apparatus as claimed in claim 20, in which the size of the drop is determined at essentially zero magnetization of the capillary tube and at a level of magnetization at which the capillary tube is magnetized to saturation or above and in which the means for determining the size of a drop comprises means for determining the drop volume.

22. Apparatus as claimed in claim 20, in which the means for determining the size of the drop comprises means for determining the drop volume that includes means for determining the change between the volume of the drop with a magnetic field applied to the capillary tube and the volume of the drop without a magnetic field applied and for relating said change with the content in the drops of the susceptible ion.

23. Apparatus as claimed in claim 20 in which the means for determining the size of the drop comprises means for determining the drop volume and that includes means for determining the change between the volume of the drop with a magnetic field applied to the capillary tube and the volume of the drop without a magnetic field applied thereto and for relating said change to the susceptibility of the ion.

24. Apparatus as in claim 20 in which the capillary tip is flat and polished.

25. Apparatus as in claim 20 in which the capillary tip has a conical geometry.

26. Apparatus as in claim 20 in which the capillary tip has a spherical geometry.

27. Apparatus as in claim 20 in which the capillary tube is made of a magnetically permeable material around which is wrapped an electric conductor.

28. Apparatus for determining the fractional content in a liquid solution of an ion susceptible to a gradient field of an applied force field, that comprises, a capillary tube to receive the solution which emits as drops from the tip thereof, means for applying a gradient field of an applied force field to the region of said tip of the capillary tube, means for feeding the solution into the tube slowly so that a drop will form at the capillary tube tip and separate therefrom, the size of the drop being variable as a function of the susceptibility of the contained ion, the content of the ion in solution and the intensity of the applied force field gradient at the capillary tube tip, and means for determining the size of a drop of the solution emitted from the capillary tip at one value of the applied force field gradient and the size of a drop of the solution emitted from the capillary tube tip at another value of the applied force field gradient and for relating any difference in the size of the drop at said one value of applied force field gradient and the size of a drop at said another value of applied force field gradient to the content of the ion in solution.

29. Apparatus as in claim 28 in which the capillary tip is flat and polished.

30. Apparatus as in claim 28 in which the capillary tip has a conical geometry.

31. Apparatus as in claim 28 in which the capillary tip has a spherical geometry.

32. A method of determining the fractional content in a liquid solution of an ion susceptible to a gradient field of an applied force field, that comprises, forming at the end of a capillary tube a first drop of the solution containing the ion with no applied gradient field and noting at least one of the volume and equivalently the weight of the first drop that detaches from the capillary tube, forming at the end of the capillary tube a second drop of the solution containing the ion with a gradient field of an applied force field in the region occupied by the second drop and noting at least one of the volume and equivalently the weight of the second drop that detaches from the capillary tube in the presence of the gradient field, the drops being formed by feeding the solution into the capillary tube slowly so that the drops will form consistently at the capillary tip, the volume and weight of the drops being different for a condition wherein they are formed in the presence of the force field in the region occupied by the drops than when there is no applied field, determining any change in at least one of the volume and weight between the first drop and second drop, and correlating said change with the content in the drops of the susceptible ion.

* * * * *